US008775215B1

(12) United States Patent  
Butler et al.

(10) Patent No.: US 8,775,215 B1  
(45) Date of Patent: Jul. 8, 2014

(54) SYSTEMS AND METHODS FOR INSURANCE CLAIMS SETTLEMENTS

(75) Inventors: James P. Butler, Rimrock, AZ (US); Connie T. Niebling, Fountain Hills, AZ (US); Sha L. Appenzeller, El Mirage, AZ (US); Ericka K. Fuhrmann, Glendale, AZ (US)

(73) Assignee: USAA United Services Automobile Assoc., San Antonio, TX (US)

( * ) Notice: Subject to any disclaimer, the term of this patent is extended or adjusted under 35 U.S.C. 154(b) by 1068 days.

(21) Appl. No.: 12/177,544

(22) Filed: Jul. 22, 2008

(51) Int. Cl.  
*G06Q 40/00* (2012.01)

(52) U.S. Cl.  
USPC .................................................. 705/4

(58) Field of Classification Search  
CPC ........ G06Q 40/00; G06Q 20/22; G06Q 20/29  
USPC ................. 705/1–100; 205/1–30; 709/1–133; 713/195–200; 235/1–88  
See application file for complete search history.

(56) References Cited

U.S. PATENT DOCUMENTS

| 5,950,169 | A | 9/1999 | Borghesi et al. | |
| 2002/0010679 | A1* | 1/2002 | Felsher | 705/51 |
| 2002/0035488 | A1 | 3/2002 | Aquila et al. | |
| 2003/0028474 | A1* | 2/2003 | Butler | 705/37 |
| 2003/0158750 | A1 | 8/2003 | Banks et al. | |
| 2005/0075912 | A1* | 4/2005 | Bealke et al. | 705/4 |
| 2007/0156581 | A1* | 7/2007 | Imrey et al. | 705/39 |

OTHER PUBLICATIONS

AHIP staff, An Updated Survey of Health Care Claims Receipt and Processing Times, May 2006, web, 1-5.*  
Gribble, Jules et al., "Insurance: Online or On the line?" The Institute of Actuaries of Australia, Contact: AskIT! Consulting, 5 Wattle Court, Lower Templestowe VIC 3107, Australia. © 2000 The Institute of Actuaries of Australia.

* cited by examiner

*Primary Examiner* — Marissa Liu  
(74) *Attorney, Agent, or Firm* — Baker Hostetler LLP

(57) ABSTRACT

Systems and methods for insurance claims processing are provided. A system for processing insurance claims may comprise at least one subsystem that makes an automatic assignment of a project to a loss services provider via a selection of an item on a user interface, and at least one subsystem that incorporates information from a report from the loss services provider into a database without manual retyping of said information from the report.

6 Claims, 9 Drawing Sheets

SYSTEMS AND METHODS FOR INSURANCE CLAIMS SETTLEMENTS

CROSS REFERENCE TO RELATED APPLICATIONS

The patent applications below (including the present patent application) are filed concurrently and share a common title and disclosure, each of which is hereby incorporated herein by reference in its entirety:
U.S. patent application Ser. No. 12/177,558; and
U.S. patent application Ser. No. 12/177,573.

BACKGROUND

A typical process for evaluating and settling a bodily injury claim is often fraught with delays and unneeded costs. These may involve waiting for insurance claims adjusters to send to a myriad of medical care providers authorization forms to release the claimants medical records and also waiting on the often busy claims adjusters to follow up with the medical care providers to receive the requested medical records. This process is often frustrating to the claimant due to the claimant not having the feeling of any control over the process and continually having to call and follow up with the claims adjuster. This process is also costly to the insurance company as well in postage costs for mailing the medical authorizations and time spent by the claims adjusters collecting the medical bills and records.

A common practice presently is that automobile injury claims adjusters mail the injured claimants a bodily injury medical authorization with a medical care provider listing. The claimant completes the forms and then mails the forms back to the adjuster. The adjuster then writes letters to the medical care providers who send medical bills to the adjuster. The adjuster then evaluates the injury and makes a settlement offer. During the interim, the claimants call for status of their injury claim, medical care providers call for status of bill payment, and claims adjusters call and write for status of treatment, all costing time and money to the insurance company and causing added frustration to the claimant.

Thus, needed are processes and a system that addresses the above and other shortcomings of the prior art.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

In consideration of the above-identified shortcomings of the art, systems and methods for insurance claim processing are provided. For several embodiments, a system for processing insurance claims comprises at least one subsystem that makes an automatic assignment of a project to a loss services provider via a selection of an item on a user interface, and at least one subsystem that incorporates information from a report from the loss services provider into a database without manual retyping of said information from the report.

Other advantages and features of the invention are described below.

BRIEF DESCRIPTION OF THE DRAWINGS

Systems and methods for insurance claims settlements are further described with reference to the accompanying drawings in which:

DETAILED DESCRIPTION

Certain specific details are set forth in the following description and figures to provide a thorough understanding of various embodiments of the invention. Certain well-known details often associated with computing and software technology are not set forth in the following disclosure to avoid unnecessarily obscuring the various embodiments of the invention. Further, those of ordinary skill in the relevant art will understand that they can practice other embodiments of the invention without one or more of the details described below. Finally, while various methods are described with reference to steps and sequences in the following disclosure, the description as such is for providing a clear implementation of embodiments of the invention, and the steps and sequences of steps should not be taken as required to practice this invention.

Figure 1:
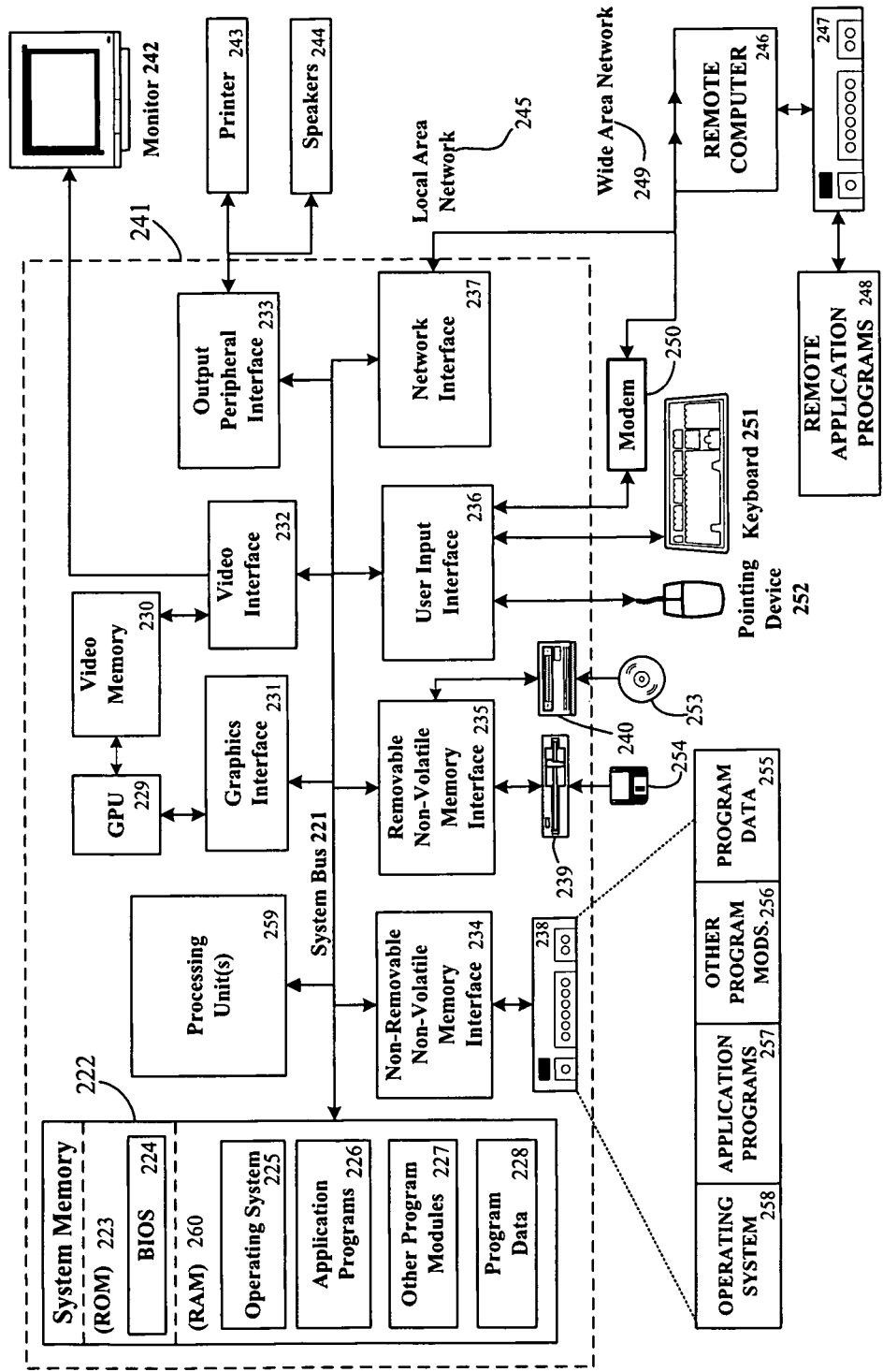
FIG. 1 is a block diagram representing an exemplary computing device suitable for use in conjunction with implementing systems and methods for insurance claims settlements.

Referring next to FIG. 1, shown is a block diagram representing an exemplary computing device suitable for use in conjunction with implementing the processes described above. For example, the computer executable instructions that carry out the processes and methods for insurance claims settlements may reside and/or be executed in such a computing environment as shown in FIG. 1. The computing system environment 220 is only one example of a suitable computing environment and is not intended to suggest any limitation as to the scope of use or functionality of the invention. Neither should the computing environment 220 be interpreted as having any dependency or requirement relating to any one or combination of components illustrated in the exemplary operating environment 220. For example a computer game console may also include those items such as those described below for use in conjunction with implementing the processes described above.

Aspects of the invention are operational with numerous other general purpose or special purpose computing system environments or configurations. Examples of well known computing systems, environments, and/or configurations that may be suitable for use with the invention include, but are not limited to, personal computers, server computers, hand-held or laptop devices, multiprocessor systems, microprocessor-based systems, set top boxes, programmable consumer electronics, network PCs, minicomputers, mainframe computers, distributed computing environments that include any of the above systems or devices, and the like.

Aspects of the invention may be implemented in the general context of computer-executable instructions, such as program modules, being executed by a computer. Generally, program modules include routines, programs, objects, components, data structures, etc. that perform particular tasks or implement particular abstract data types. Aspects of the invention may also be practiced in distributed computing environments where tasks are performed by remote processing devices that are linked through a communications network. In a distributed computing environment, program modules may be located in both local and remote computer storage media including memory storage devices.

An exemplary system for implementing aspects of the invention includes a general purpose computing device in the form of a computer 241. Components of computer 241 may include, but are not limited to, a processing unit 259, a system memory 222, and a system bus 221 that couples various system components including the system memory to the processing unit 259. The system bus 221 may be any of several types of bus structures including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus.

Computer 241 typically includes a variety of computer readable media. Computer readable media can be any available media that can be accessed by computer 241 and includes both volatile and nonvolatile media, removable and non-removable media. By way of example, and not limitation, computer readable media may comprise computer storage media and communication media. Computer storage media includes both volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can accessed by computer 241. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer readable media.

The system memory 222 includes computer storage media in the form of volatile and/or nonvolatile memory such as read only memory (ROM) 223 and random access memory (RAM) 260. A basic input/output system 224 (BIOS), containing the basic routines that help to transfer information between elements within computer 241, such as during start-up, is typically stored in ROM 223. RAM 260 typically contains data and/or program modules that are immediately accessible to and/or presently being operated on by processing unit 259. By way of example, and not limitation, FIG. 1 illustrates operating system 225, application programs 226, other program modules 227, and program data 228.

The computer 241 may also include other removable/non-removable, volatile/nonvolatile computer storage media. By way of example only, FIG. 1 illustrates a hard disk drive 238 that reads from or writes to non-removable, nonvolatile magnetic media, a magnetic disk drive 239 that reads from or writes to a removable, nonvolatile magnetic disk 254, and an optical disk drive 240 that reads from or writes to a removable, nonvolatile optical disk 253 such as a CD ROM or other optical media. Other removable/non-removable, volatile/nonvolatile computer storage media that can be used in the exemplary operating environment include, but are not limited to, magnetic tape cassettes, flash memory cards, digital versatile disks, digital video tape, solid state RAM, solid state ROM, and the like. The hard disk drive 238 is typically connected to the system bus 221 through an non-removable memory interface such as interface 234, and magnetic disk drive 239 and optical disk drive 240 are typically connected to the system bus 221 by a removable memory interface, such as interface 235.

The drives and their associated computer storage media discussed above and illustrated in FIG. 1, provide storage of computer readable instructions, data structures, program modules and other data for the computer 241. In FIG. 1, for example, hard disk drive 238 is illustrated as storing operating system 258, application programs 257, other program modules 256, and program data 255. Note that these components can either be the same as or different from operating system 225, application programs 226, other program modules 227, and program data 228. Operating system 258, application programs 257, other program modules 256, and program data 255 are given different numbers here to illustrate that, at a minimum, they are different copies. A user may enter commands and information into the computer 241 through input devices such as a keyboard 251 and pointing device 252, commonly referred to as a mouse, trackball or touch pad. Other input devices (not shown) may include a microphone, joystick, game pad, satellite dish, scanner, or the like. These and other input devices are often connected to the processing unit 259 through a user input interface 236 that is coupled to the system bus, but may be connected by other interface and bus structures, such as a parallel port, game port or a universal serial bus (USB). A monitor 242 or other type of display device is also connected to the system bus 221 via an interface, such as a video interface 232. In addition to the monitor, computers may also include other peripheral output devices such as speakers 244 and printer 243, which may be connected through a output peripheral interface 233.

The computer 241 may operate in a networked environment using logical connections to one or more remote computers, such as a remote computer 246. The remote computer 246 may be a personal computer, a server, a router, a network PC, a peer device or other common network node, and typically includes many or all of the elements described above relative to the computer 241, although only a memory storage device 247 has been illustrated in FIG. 1. The logical connections depicted in FIG. 1 include a local area network (LAN) 245 and a wide area network (WAN) 249, but may also include other networks. Such networking environments are commonplace in offices, enterprise-wide computer networks, intranets and the Internet.

When used in a LAN networking environment, the computer 241 is connected to the LAN 245 through a network interface or adapter 237. When used in a WAN networking environment, the computer 241 typically includes a modem 250 or other means for establishing communications over the WAN 249, such as the Internet. The modem 250, which may be internal or external, may be connected to the system bus 221 via the user input interface 236, or other appropriate mechanism. In a networked environment, program modules depicted relative to the computer 241, or portions thereof, may be stored in the remote memory storage device. By way of example, and not limitation, FIG. 1 illustrates remote application programs 248 as residing on memory device 247. It will be appreciated that the network connections shown are exemplary and other means of establishing a communications link between the computers may be used.

It should be understood that the various techniques described herein may be implemented in connection with hardware or software or, where appropriate, with a combination of both. Thus, the methods and apparatus of the invention, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computer, the machine becomes an apparatus for practicing the invention. In the case of program code execution on programmable computers, the computing device generally includes a processor, a storage medium readable by the processor (including volatile and non-volatile memory and/or storage elements), at least one input device, and at least one output device. One or more programs that may implement or utilize the processes described in connection with the invention, e.g., through the use of an API, reusable controls, or the like. Such programs are preferably implemented in a high level procedural or object oriented programming language to communicate with a computer system. However, the program(s) can be implemented in assembly or machine language, if desired. In any case, the language may be a compiled or interpreted language, and combined with hardware implementations.

Although exemplary embodiments may refer to utilizing aspects of the invention in the context of one or more stand-alone computer systems, the invention is not so limited, but rather may be implemented in connection with any computing environment, such as a network or distributed computing environment. Still further, aspects of the invention may be implemented in or across a plurality of processing chips or devices, and storage may similarly be effected across a plurality of devices. Such devices might include personal computers, network servers, handheld devices, supercomputers, or computers integrated into other systems such as automobiles and airplanes.

Figure 2:
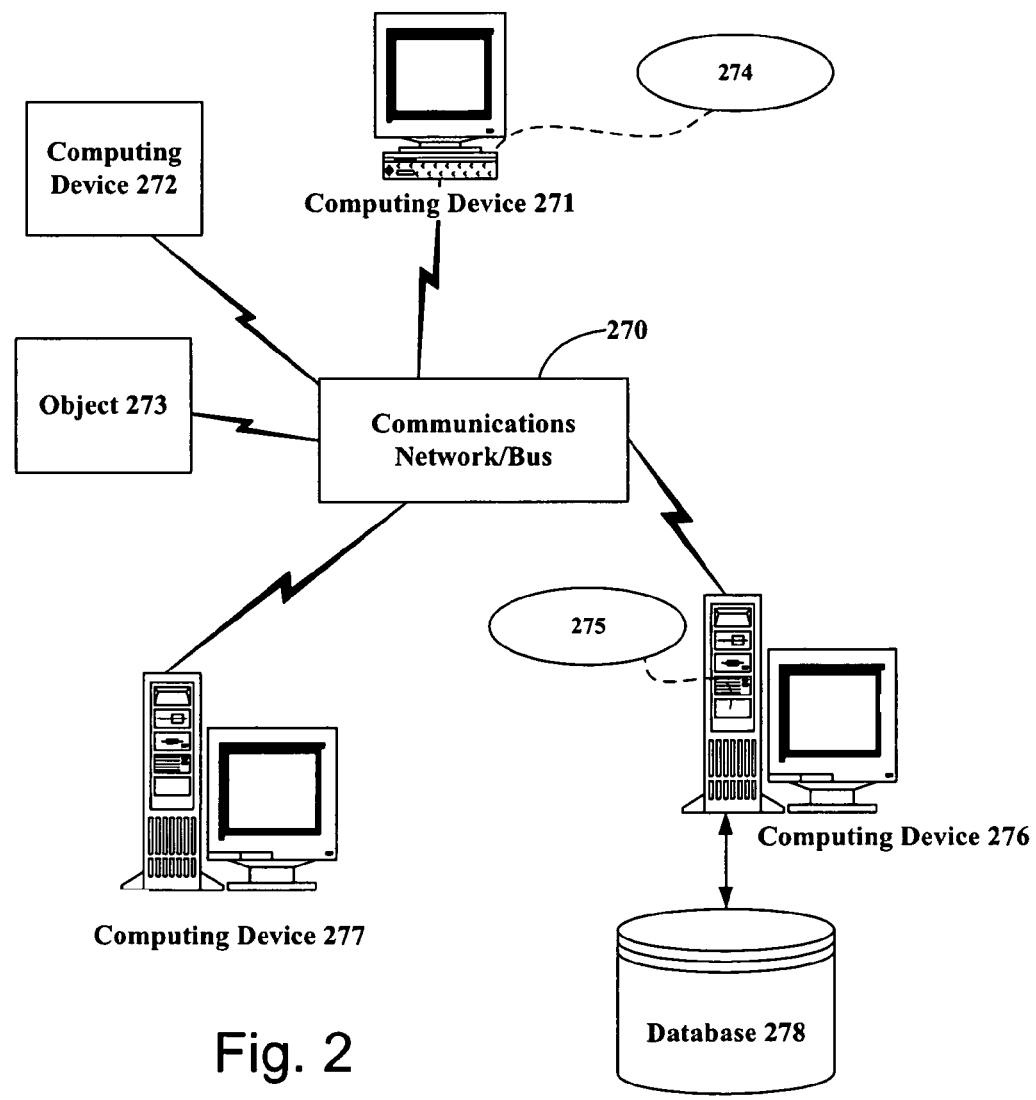
FIG. 2 illustrates an exemplary networked computing environment in which many computerized processes may be implemented to perform insurance claims settlements.

Referring next to FIG. 2, shown is an exemplary networked computing environment in which many computerized processes may be implemented to perform the processes described above. For example, parallel computing may be part of such a networked environment with various clients on the network of FIG. 2 using and/or implementing systems and methods for insurance claims settlements. One of ordinary skill in the art can appreciate that networks can connect any computer or other client or server device, or in a distributed computing environment. In this regard, any computer system or environment having any number of processing, memory, or storage units, and any number of applications and processes occurring simultaneously is considered suitable for use in connection with the systems and methods provided.

Distributed computing provides sharing of computer resources and services by exchange between computing devices and systems. These resources and services include the exchange of information, cache storage and disk storage for files. Distributed computing takes advantage of network connectivity, allowing clients to leverage their collective power to benefit the entire enterprise. In this regard, a variety of devices may have applications, objects or resources that may implicate the processes described herein.

FIG. 2 provides a schematic diagram of an exemplary networked or distributed computing environment. The environment comprises computing devices 271, 272, 276, and 277 as well as objects 273, 274, and 275, and database 278. Each of these entities 271, 272, 273, 274, 275, 276, 277 and 278 may comprise or make use of programs, methods, data stores, programmable logic, etc. The entities 271, 272, 273, 274, 275, 276, 277 and 278 may span portions of the same or different devices such as PDAs, audio/video devices, MP3 players, personal computers, etc. Each entity 271, 272, 273, 274, 275, 276, 277 and 278 can communicate with another entity 271, 272, 273, 274, 275, 276, 277 and 278 by way of the communications network 270. In this regard, any entity may be responsible for the maintenance and updating of a database 278 or other storage element.

This network 270 may itself comprise other computing entities that provide services to the system of FIG. 2, and may itself represent multiple interconnected networks. In accordance with an aspect of the invention, each entity 271, 272, 273, 274, 275, 276, 277 and 278 may contain discrete functional program modules that might make use of an API, or other object, software, firmware and/or hardware, to request services of one or more of the other entities 271, 272, 273, 274, 275, 276, 277 and 278.

It can also be appreciated that an object, such as 275, may be hosted on another computing device 276. Thus, although the physical environment depicted may show the connected devices as computers, such illustration is merely exemplary and the physical environment may alternatively be depicted or described comprising various digital devices such as PDAs, televisions, MP3 players, etc., software objects such as interfaces, COM objects and the like.

There are a variety of systems, components, and network configurations that support distributed computing environments. For example, computing systems may be connected together by wired or wireless systems, by local networks or widely distributed networks. Currently, many networks are coupled to the Internet, which provides an infrastructure for widely distributed computing and encompasses many different networks. Any such infrastructures, whether coupled to the Internet or not, may be used in conjunction with the systems and methods provided.

A network infrastructure may enable a host of network topologies such as client/server, peer-to-peer, or hybrid architectures. The "client" is a member of a class or group that uses the services of another class or group to which it is not related. In computing, a client is a process, i.e., roughly a set of instructions or tasks, that requests a service provided by another program. The client process utilizes the requested service without having to "know" any working details about the other program or the service itself. In a client/server architecture, particularly a networked system, a client is usually a computer that accesses shared network resources provided by another computer, e.g., a server. In the example of FIG. 2, any entity 271, 272, 273, 274, 275, 276, 277 and 278 can be considered a client, a server, or both, depending on the circumstances.

A server is typically, though not necessarily, a remote computer system accessible over a remote or local network, such as the Internet. The client process may be active in a first computer system, and the server process may be active in a second computer system, communicating with one another over a communications medium, thus providing distributed functionality and allowing multiple clients to take advantage of the information-gathering capabilities of the server. Any software objects may be distributed across multiple computing devices or objects.

Client(s) and server(s) communicate with one another utilizing the functionality provided by protocol layer(s). For example, HyperText Transfer Protocol (HTTP) is a common protocol that is used in conjunction with the World Wide Web (WWW), or "the Web." Typically, a computer network address such as an Internet Protocol (IP) address or other reference such as a Universal Resource Locator (URL) can be used to identify the server or client computers to each other. The network address can be referred to as a URL address. Communication can be provided over a communications medium, e.g., client(s) and server(s) may be coupled to one another via TCP/IP connection(s) for high-capacity communication.

In light of the diverse computing environments that may be built according to the general framework provided in FIG. 2 and the further diversification that can occur in computing in a network environment such as that of FIG. 2, the systems and methods provided herein cannot be construed as limited in any way to a particular computing architecture. Instead, the invention should not be limited to any single embodiment, but rather should be construed in breadth and scope in accordance with the appended claims.

Figure 3:
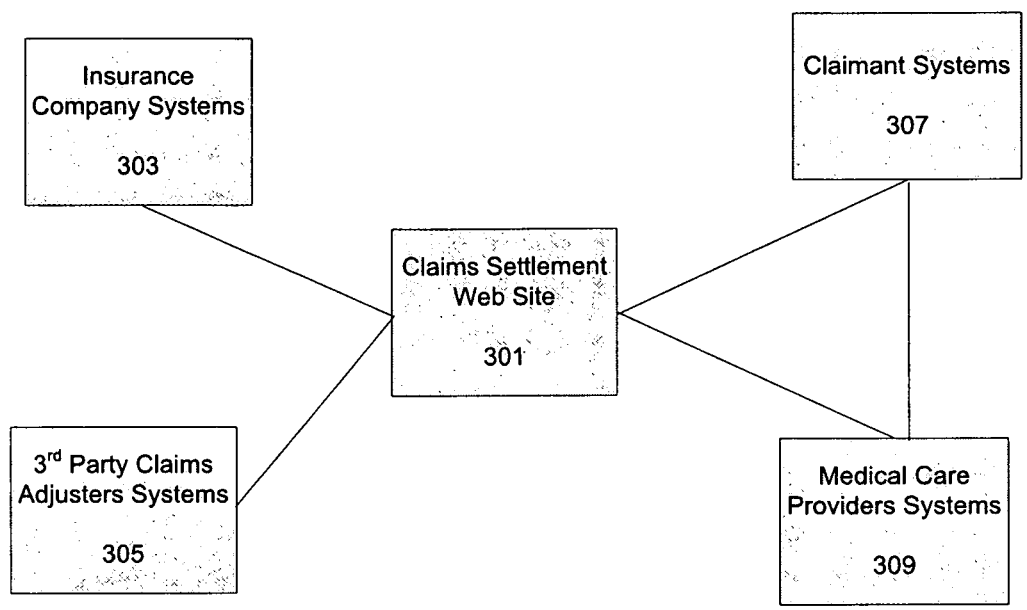
FIG. 3 is a bock diagram illustrating an exemplary system for insurance claims settlements.

Referring next to FIG. 3, shown is a bock diagram illustrating an exemplary system for insurance claims settlements. Shown is a block representing the claims settlement web site 301, a block representing the insurance company's computer and communications systems 303, a block representing any $3^{rd}$ party claims adjuster's computer and communications systems 305, a block representing the claimant's computer and communications systems 307, and a block representing the medical care provider's computer and communications systems 309.

The insurance company 303 may, for example, be an entity that provides insurance to an insured person or entity. The claimant 307 may be an entity or person that has or makes a claim against the insured person or entity for an injury or other harm that the insurance policy provided by the insurance company 303 to the insured may or may not cover. The insurance company 303 may be the seller of an insurance policy held by the insured or the insurance company 303 may be an entity that provides insurance services or insurance policy services to the insured. For example, if the insurance policy provided by the insurance company 303 is an automobile policy and the insured is involved in an auto accident, a party harmed in the auto accident may perhaps make a claim against the insured for injuries. This person making the claim is considered a claimant 307 (whether or not the automobile insurance policy technically or legally covers the insured for such claims). Also, the claimant 307 may be the same as person or entity as the insured in cases where the insured is making a claim to the insurance company 303 directly that the insurance policy provided by the insurance company 303 covers the insured's own damages.

$3^{rd}$ party claims adjusters are insurance claims adjusters that are separate legal entities than the insurance company, for example. $3^{rd}$ party claims adjusters may work closely with the insurance company 305 to evaluate and settle an insurance claim. However, the insurance company may have its own internal claims adjusters as well. Therefore, $3^{rd}$ party claims adjusters systems are not a necessary or essential component of the system described in FIG. 3, but systems accommodating them within the claims settlement process are a desirable feature.

The insurance company 303, the claims settlement web site 301 (or entity hosting the web site), $3^{rd}$ party claims adjuster's 305, the claimant 307, and medical care providers 309 may have any number of associated computing systems that may comprise one or more computing devices. For example, a computing device may allow a user at the insurance company 301 to interact with the computing device(s) of the other entities in FIG. 3, (e.g., such as through the Internet). The computing device(s) may have one or more processors, storage (e.g., storage devices, memory, etc.), and software modules. The computing device(s), including its processor(s), storage, and software modules, may be used in the performance of the techniques and operations described herein. Information associated with the user may be stored in storage or other storage such as internal storage, for example. The lines connecting the entities in FIG. 3 represent operable lines of communication (including electronic communication) between the entities.

Examples of software modules may include modules for identifying and authenticating a user, generating web page content for display over the Internet or other communications network 303, and receiving requests and instructions from a user, described further herein. While specific functionality is described herein as occurring with respect to specific modules, the functionality may likewise be performed by more, fewer, or other modules. An example computing device and its components are described in more detail with respect to FIG. 1.

Figure 4:
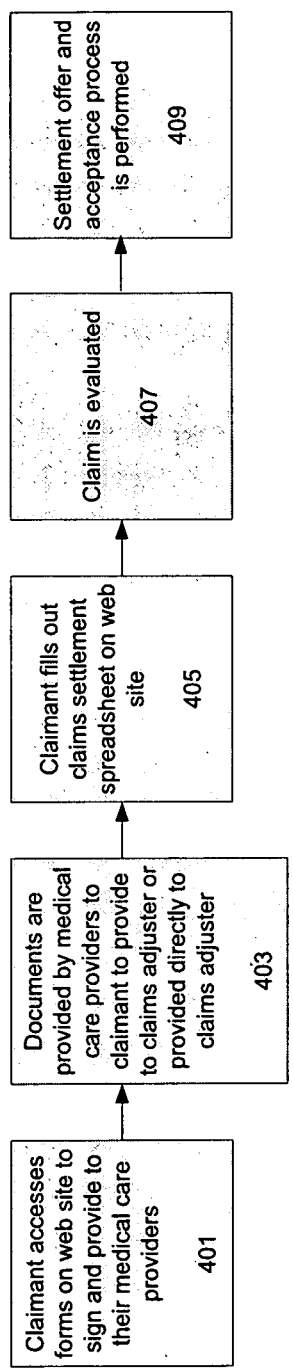
FIG. 4 is a flow chart illustrating an exemplary process for insurance claims settlements.

Referring next to FIG. 4, shown is a flow chart illustrating an exemplary process for insurance claims settlements. In one embodiment, a claimant accesses 401 forms on the claim settlement web site to sign and provide to their medical care providers. These forms may include those such as authorizations to release medical records and medical bills to the insurance company and/or $3^{rd}$ party claims adjusters. These forms may be printed out by the claimant, signed and then mailed by the claimant to the appropriate medical care providers. However, these forms may also be electronically signed and electronically provided by the claimant to the medical care providers saving time and expense. The method of electronic signature of these documents and other documents described herein may be by any number of currently available methods of electronic signature known in the art. Also, the method of electronic communication of these documents to the medical care providers and other documents described herein may be via email, upload or downloading over a computer network, fax, text messaging, wireless transmission or other electronic communication means. In one embodiment the documents are viewed, electronically signed, and transmitted via one or more sessions on the claims settlement web site 301, or via services provided by the claims settlement web site. Also, when a claimant visits the claims settlement web site 301, instructions on how to complete and send the medical authorization forms as well as a general introduction and other instructions may be made available to the claimant via help pages integrated into the web site 301 and/or a video or audio clips providing such information.

Documents such as medical records and medical bills are then provided 403 by the medical care providers to the claimant to provide to the claims adjuster and/or insurance company or the documents are provided directly to claims adjuster and/or insurance company. A copy of these documents may also be sent by the medical care providers to the claimant for their records. Such instructions on where and to whom to send copies may be included on the authorizations sent to the medical care providers by the claimant.

Once the copies of medical documents are sent by the medical care providers or claimant, the claimant may then log on to the claims settlement web site 301 and complete 405 a claims settlement spreadsheet.

Figure 5:
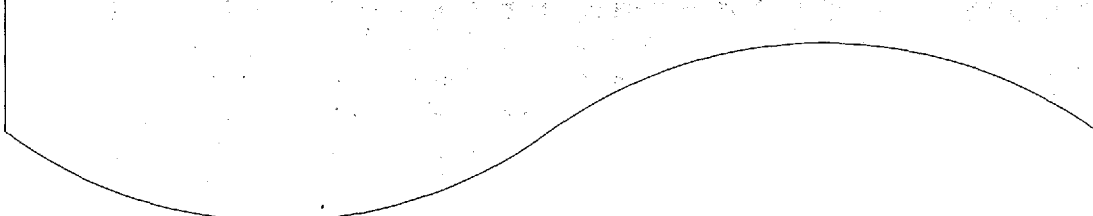
FIG. 5 is a diagram of an example spreadsheet component of an interface for an insurance claim settlements system.

Referring next to FIG. 5, shown is a diagram of an example claims settlement spreadsheet component 501 of a web interface for an insurance claim settlements system. Among other possible sections, the claims settlement spreadsheet component 501 may comprise a medical provider itemization section 503, a wage loss section, and an electronic signature/submission section 511. The medical provider itemization section 503 may comprise, among other possible subsections, a subsection to input the provider type 505 (with a number of provider types provided as choices in a drop down menu 523, for example), a subsection to input the provider name 507, and a subsection to fill in the billed amount. There may also be total billed amount subsection 525 where a total of the amounts entered in the billed amount subsection 509 appear. The wage loss section 511 may comprise, among other possible subsections, a subsection to input the employer name 513, a subsection to input the hourly wage 515, a subsection to input the hours missed 517 and a total wage loss subsection 519. The total wage loss may be automatically computed based upon the hourly wage and hours missed values entered. The electronic signature/submission section may include a statement concerning the claim to which the claimant agrees by electronically signing 521 the completed claims settlement spreadsheet component 501.

Figure 6:
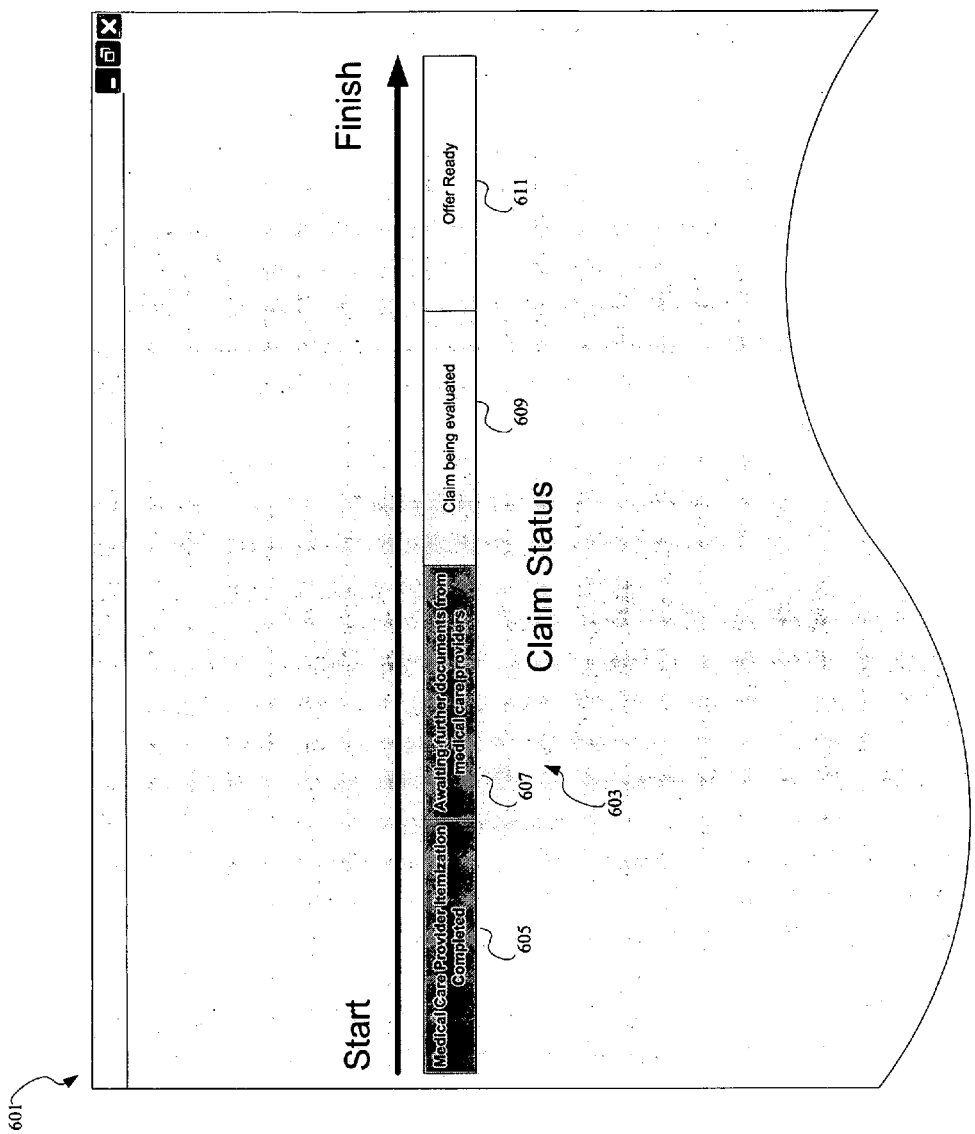
FIG. 6 is a diagram of an example claim status component of an interface for an insurance claim settlements system.

Referring back to FIG. 4, once the claimant fills out and submits 405 the claims settlement spreadsheet on the web site 301, the claim is evaluated 407 by the insurance company and/or claims adjuster. The claimant and other authorized users of the web site may at any time log on to the claims settlement web site and 301 and view the status of the claim. Referring next to FIG. 6, shown is a diagram of an example claim status component 601 of the interface for the example insurance claim settlements system. The claim status component may comprise a color coded status bar 603 on which various stages 605, 607, 609, 611 of claim status may appear. For example, as each stage is entered, the color or shading of that stage will change. In the example provided in FIG. 6, the medical care provider itemization has been completed thus that stage 605 has changed from a lighter shade to a darker shade, but there are still documents from medical care providers that have yet to be received. Therefore, the stage of "awaiting further documents from medical care providers" 607 has been entered and the color of that stage has also been changed from a lighter shade to a darker shade. The next stage of "claim being evaluated" 609 has yet to be entered since all the medical documents have not been received. Therefore, its color has not yet changed to the darker shade.

Figure 7:
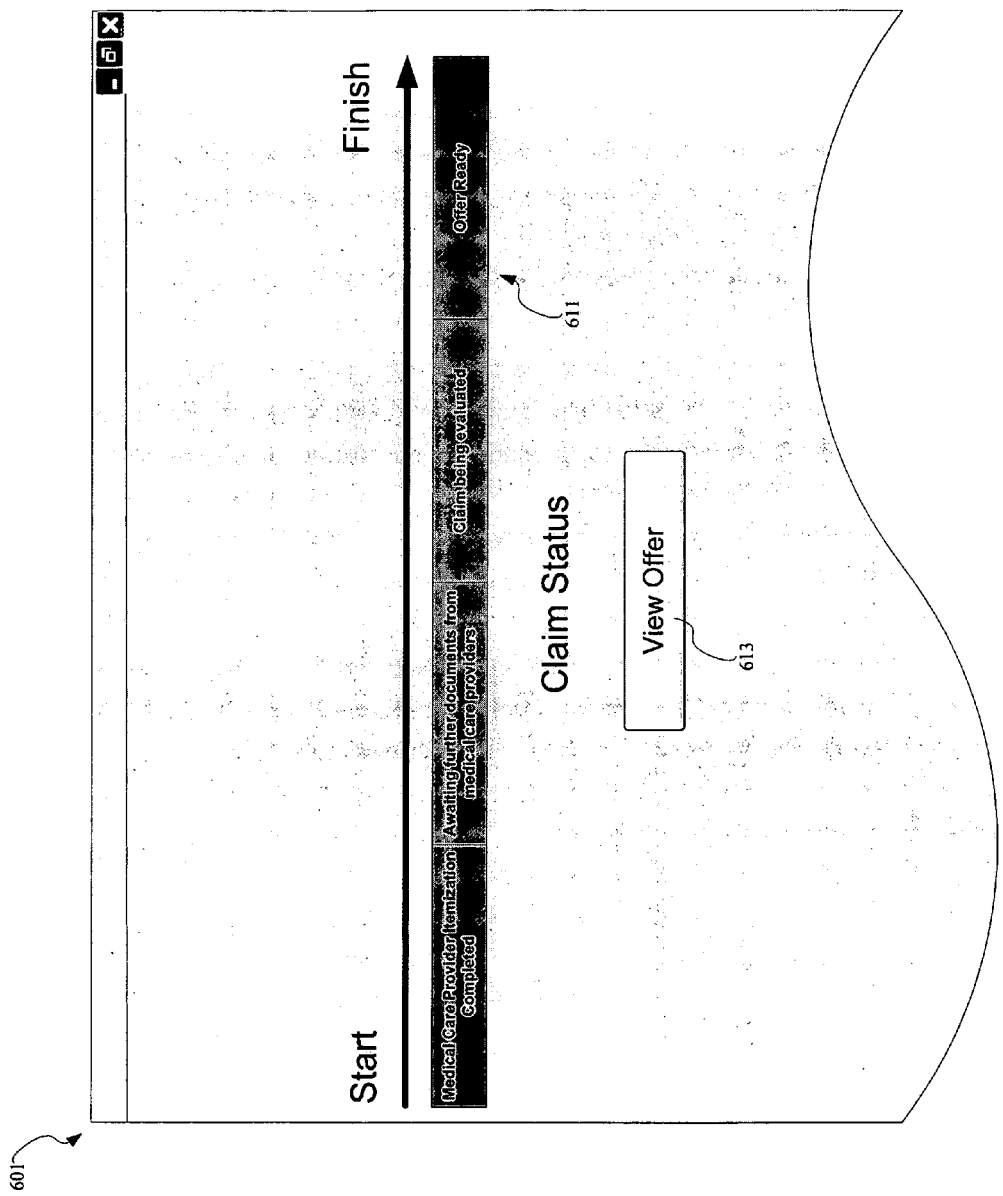
FIG. 7 is a diagram of example claim status and "view offer" components of an interface for an insurance claim settlements system.

Referring back to FIG. 4, if it is determined that a settlement offer is in order, the settlement offer and acceptance process is entered 409. Referring next to FIG. 7, once the settlement offer is ready, the "offer ready" stage 611 color will have changed to the darker shade (as well as the previous stages), and a "view offer" button 613 will appear on the web page 601. The offer may also be viewed by other means such as clicking on a link to the offer in an email notice or other electronic messaging system.

Figure 8:
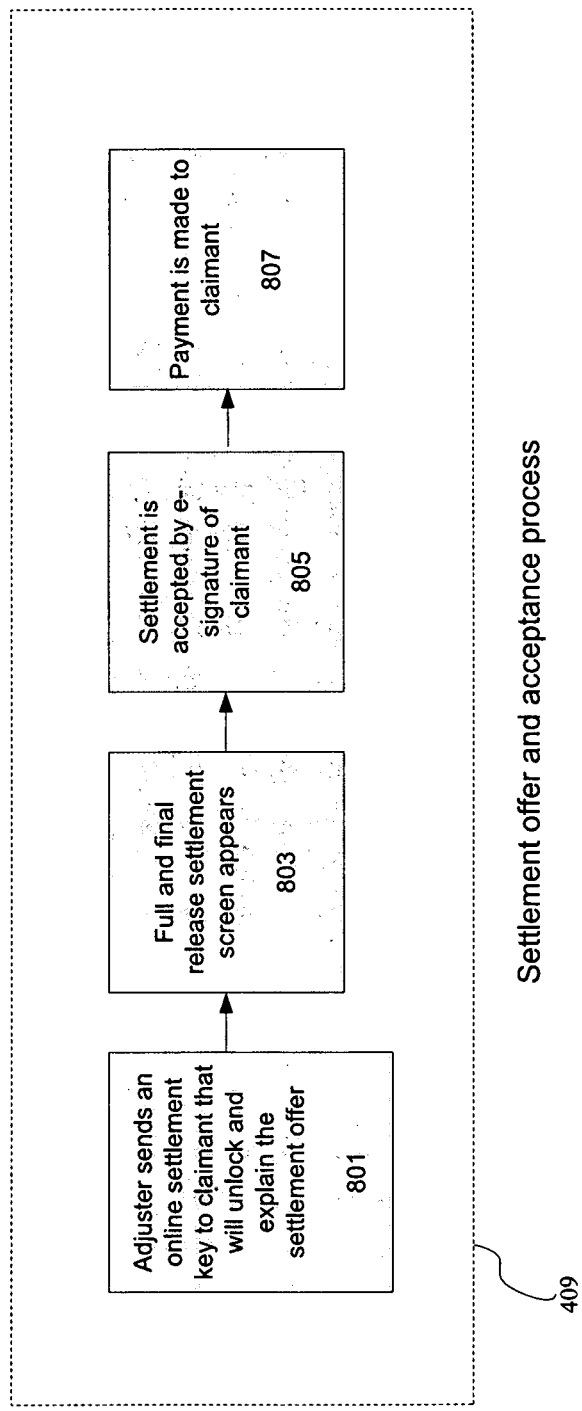
FIG. 8 is a flow chart illustrating an exemplary settlement offer and acceptance process for insurance claims settlements.
Figure 9:
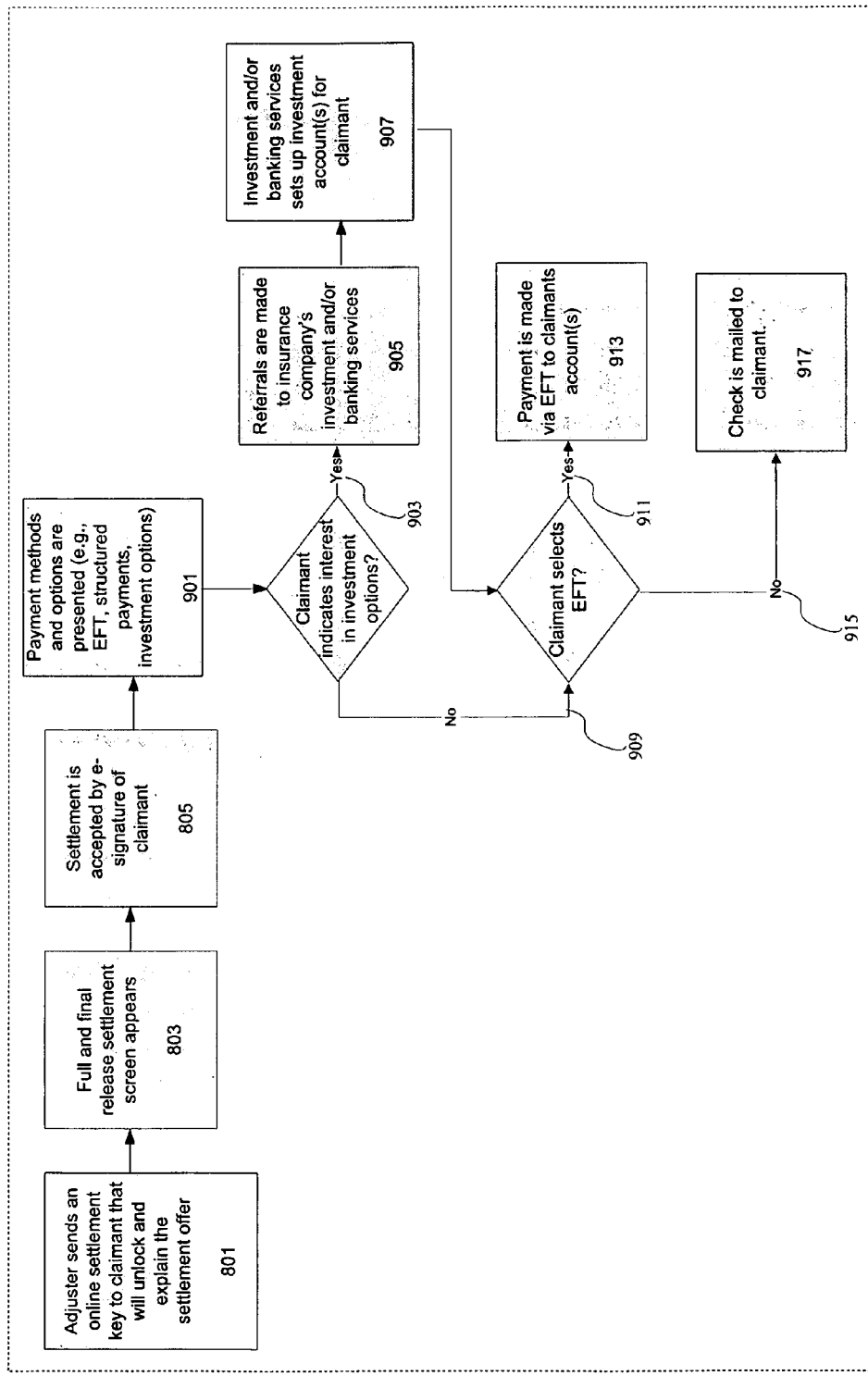
FIG. 9 is a flow chart illustrating an exemplary additional settlement offer and acceptance process for insurance claims settlements.

Referring next to FIGS. 8 and 9 shown are flow charts illustrating exemplary settlement offer and acceptance processes 409 for insurance claims settlements. In one embodiment, the claims adjuster may send 801 an online settlement key to claimant that will unlock and explain the settlement offer. This key may be sent via various means of electronic messaging such as email, text messaging, instant messaging and so forth. The claimant may then use this key to authenticate that the claimant is authorized to view the settlement offer. For example, the claimant may enter the key into an authentication system that is part of the claims settlement web site to view the offer. However, other authentication systems are contemplated both as part of and separate from the claims settlement web site. A full and final release settlement screen may then appear 803 as part of the settlement offer which the claimant may electronically sign in order to accept 805 the settlement and release the insurance company and/or insured from further liability. Payment may then be made 901 to the claimant via various means. For example, as shown in FIG. 9, various pay payment methods and options may be presented 901 (e.g., electronic funds transfer, structured payments, investment options) to the claimant on via the claims settlement web site 301 or other electronic messaging. This may occur before, immediately after, or soon after the settlement offer is accepted. If the claimant indicates an interest in investment options 903, immediate online referrals may be made to insurance company's own investment and/or banking services or other sponsored investment or banking services, for example. The investment and/or banking services may then create or set up 907 one or more investment or banking accounts indicated by the claimant. All or part of the settlement amount may then be used to fund any new investment account(s) set up or be deposited into existing investment or banking accounts as indicated by the claimant. The selection, creation, funding or depositing into the investment and/or banking accounts may be fully automated using electronic funds transfer (EFT) and may also be completed via the claims settlement web site as part of the settlement offer and acceptance process 409 or via a link from the claims settlement web site to other investment and/or banking services web sites.

If the claimant selects EFT as a payment method 911, payment is made via EFT 913 to the claimant's account(s) (whether they are existing accounts or those newly created in the process described above to be funded by the settlement funds). Also, the claimant may choose to select different portions of the settlement to go to different accounts. If the claimant does not select EFT 915, then payment is made by other means such the mailing 917 of a check, for example.

It is noted that the foregoing examples have been provided merely for the purpose of explanation and are in no way to be construed as limiting of the present invention. In particular, the foregoing examples may have been provided partly in the context of bodily injury claims, however the same concepts may also be applied and are contemplated herein to other possible types of damage to a claimant and other areas of possible insurance coverage. While the invention has been described with reference to various embodiments, it is understood that the words which have been used herein are words of description and illustration, rather than words of limitations. Further, although the invention has been described herein with reference to particular means, materials and embodiments, the invention is not intended to be limited to the particulars disclosed herein; rather, the invention extends to all functionally equivalent structures, methods and uses, such as are within the scope of the appended claims. Those skilled in the art, having the benefit of the teachings of this specification, may effect numerous modifications thereto and changes may be made without departing from the scope and spirit of the invention in its aspects.

What is claimed is:

1. A system for settling insurance claims comprising:
   at least one hardware-implemented computing system that provides documentation via a website to a claimant to provide to one or more medical care providers, said documentation required by said one or more medical care providers in order to release records associated with said claimant, and said documentation configured to be electronically signed by said claimant before electronic submission to said one or more medical care providers;
   at least one hardware-implemented computing system that transmits a signed electronic document to said one or more medical care providers, said signed electronic document being signed by said claimant, and said signed electronic document releasing records comprising medical records and medical bills to said system for settling insurance claims;
   at least one hardware-implemented computing system that receives, in response to said electronically transmitted signed electronic document, one or more of said records associated with said claimant; and
   at least one hardware-implemented computing system that provides a settlement offer to said claimant based at least in part on said one or more records received, said settlement offer provided on said website.

2. The system of claim 1 wherein said at least one hardware-implemented computing system that provides aid documentation and said at least one subsystem that provides said settlement offer are configured to provide said documentation and provide said settlement offer electronically within an account said claimant accesses via a computer network.

3. A method for settling insurance claims comprising:
   providing documentation, by a hardware-implemented computing system, via a website to a claimant to provide to one or more medical care providers, said documentation required by said one or more medical care providers in order to release records associated with said claimant, and said documentation configured to be electronically signed by said claimant before electronic submission to said one or more medical care providers;
   transmitting, by the hardware-implemented computing system, a signed electronic document to said one or more medical care providers, said signed electronic document being signed by said claimant, and said signed electronic document releasing records comprising medical records and medical bills for settling an insurance claim;
   receiving, by the hardware-implemented computing system, in response to said electronically transmitted signed electronic document, one or more of said records associated with said claimant; and
   providing, by the hardware-implemented computing system, a settlement offer to said claimant based at least in part on said one or more records received, said settlement offer provided on said website.

4. The method of claim 3 wherein said providing of said documentation and said providing of said settlement offer are performed electronically within an account said claimant accesses via a computer network.

5. A non-transitory computer-readable medium comprising computer-readable instructions for settling insurance claims, said computer-readable instructions comprising instructions for:
   providing documentation via a website to a claimant to provide to one or more medical care providers, said documentation required by said one or more medical care providers in order to release records associated with said claimant, and said documentation configured to be electronically signed by said claimant before electronic submission to said one or more medical care providers;
   transmitting a signed electronic document to said one or more medical care providers, said signed electronic document being signed by said claimant, and said signed electronic document releasing records comprising medical records and medical bills for settling an insurance claim;
   receiving, in response to said electronically transmitted signed electronic document, one or more of said records associated with said claimant; and
   providing a settlement offer to said claimant based at least in part on said one or more records received, said settlement offer provided on said website.

6. The non-transitory computer-readable medium of claim 5 wherein the computer readable instructions for providing of said documentation and said computer readable instructions for providing of said settlement offer comprise computer readable instructions for performing said providing of said documentation and providing of said settlement offer within an account said claimant accesses via a computer network.

* * * * *